(12) United States Patent
Castorina et al.

(10) Patent No.: US 12,397,033 B2
(45) Date of Patent: Aug. 26, 2025

(54) **COMPOSITION COMPRISING EXTRACTS OF *EUCOMMIA ULMOIDES, CROCUS SATIVUS* AND/OR *MAGNOLIA OFFICINALIS* AND THE USE THEREOF IN THE TREATMENT OF SLEEP DISORDERS**

(71) Applicant: BIOFARMA S.R.L., Mereto di Tomba (IT)

(72) Inventors: Sebastiano Maurizio Castorina, Gallarate (IT); Arianna Vanelli, Gallarate (IT); Alessandro Taddei, Gallarate (IT); Stefania Murzilli, Gallarate (IT)

(73) Assignee: BIOFARMA S.R.L., Mereto di Tomba (IT)

( * ) Notice: Subject to any disclaimer, the term of this patent is extended or adjusted under 35 U.S.C. 154(b) by 830 days.

(21) Appl. No.: 17/610,422

(22) PCT Filed: Jun. 5, 2020

(86) PCT No.: PCT/IB2020/055303
§ 371 (c)(1),
(2) Date: Nov. 10, 2021

(87) PCT Pub. No.: WO2020/245779
PCT Pub. Date: Dec. 10, 2020

(65) Prior Publication Data
US 2022/0218779 A1    Jul. 14, 2022

(30) Foreign Application Priority Data
Jun. 6, 2019 (IT) .................. 102019000008259

(51) Int. Cl.
| | | |
|---|---|---|
| *A61K 36/88* | (2006.01) |
| *A61K 9/24* | (2006.01) |
| *A61K 31/05* | (2006.01) |
| *A61K 31/11* | (2006.01) |
| *A61K 33/08* | (2006.01) |
| *A61K 36/46* | (2006.01) |
| *A61K 36/575* | (2006.01) |
| *A61P 25/20* | (2006.01) |

(52) U.S. Cl.
CPC .............. *A61K 36/88* (2013.01); *A61K 9/209* (2013.01); *A61K 31/05* (2013.01); *A61K 31/11* (2013.01); *A61K 33/08* (2013.01); *A61K 36/46* (2013.01); *A61K 36/575* (2013.01); *A61P 25/20* (2018.01)

(58) Field of Classification Search
None
See application file for complete search history.

(56) References Cited

U.S. PATENT DOCUMENTS

2002/0076456 A1    6/2002    Stogniew et al.

FOREIGN PATENT DOCUMENTS

| CN | 104623541 A | 5/2015 |
| CN | 108478749 A | 9/2018 |
| CN | 109363026 A | 2/2019 |
| JP | 2014024800 A | 2/2014 |

OTHER PUBLICATIONS

Lopresti et al. (2021) Sleep Medicine 86: 7-18. (Year: 2021).*
Milajerdi et al. (2018) Complementary Therapies in Medicine, 41: 196-202. (Year: 2018).*
Qu et al. (2012) Brit. J. Pharmacol. 167: 587-598. (Year: 2012).*

* cited by examiner

*Primary Examiner* — Russell G Fiebig
(74) *Attorney, Agent, or Firm* — James S. Keddie; Bozicevic, Field & Francis LLP

(57) ABSTRACT

The present invention relates to a composition comprising a mixture comprising or, alternatively, consisting of (a) an extract of *Eucommia ulmoides* and at least one among (b.1) saffron comprising safranal and (b.2) an extract of *Magnolia officinalis* and/or *Magnolia champaca* comprising honokiol, or the mixture thereof, as active components. Furthermore, the present invention relates to an innovative formulation of said composition for the modulated release of said active components. Lastly, the present invention relates to said composition for use in a method for the treatment of sleep cycle dysfunction, in particular both of disorders in the NON-REM stage of sleep and of disorders in the REM stage of deep sleep.

12 Claims, 1 Drawing Sheet

|  |  | VISIT 1 | VISIT 2 | VISIT 3 | VISIT 4 |
|---|---|---|---|---|---|
|  |  | Day 1 | Day 14 Contact by telephone | Day 28 | Day 35 Contact by telephone |
| Verification of the inclusion/exclusion criteria |  | x |  |  |  |
| Informed consent |  | x |  |  |  |
| Clinical history and anamnesis |  | x |  |  |  |
| Objective examination |  | x |  | x |  |
| Vital signs |  | x |  | x |  |
| Weight, height, BMI |  | x |  | x |  |
| Pregnancy test (urine) |  | x |  |  |  |
| Questionnaires/Tests: |  |  |  |  |  |
| Insomnia Severity Index (ISI) | Autosum | x |  | x |  |
| Pittsburg Sleep Quality Index (PSQI) | Autosum | x |  | x |  |
| Pre-sleep Arousal Scale (PSAS) | Autosum | x | x | x |  |
| VAS for product satisfaction | Autosum |  |  | x |  |
| Sleep diary | Autosum |  |  | x |  |
| Delivery of the product |  | x | x |  |  |
| Compliance evaluation |  |  |  | x |  |
| Concomitant therapies |  | x | x | x | x |
| Collection of the product |  |  |  | x |  |
| AE/SAE |  | x | x | x | x |

COMPOSITION COMPRISING EXTRACTS OF *EUCOMMIA ULMOIDES*, *CROCUS SATIVUS* AND/OR *MAGNOLIA OFFICINALIS* AND THE USE THEREOF IN THE TREATMENT OF SLEEP DISORDERS

CROSS-REFERENCE TO RELATED APPLICATIONS

This application is a § 371 national phase of International Application No. PCT/IB2020/055303, filed on Jun. 5, 2020, which claims the benefit of Italian Application No. 102019000008259, filed on Jun. 6, 2019, all of which applications are incorporated by reference herein.

The present invention relates to a composition comprising a mixture comprising or, alternatively, consisting of (a) an extract of *Eucommia ulmoides* and at least one among (b.1) saffron comprising safranal and (b.2) an extract of *Magnolia officinalis* and/or *Magnolia champaca* comprising honokiol, or the mixture thereof, as active components. Furthermore, the present invention relates to an innovative formulation of said composition for the modulated release of said active components. Lastly, the present invention relates to said composition for use in a method for the treatment of sleep cycle dysfunction, in particular both of disorders in the NON-REM stage of sleep and of disorders in the REM stage of deep sleep.

Sleep is defined as a state of rest opposed to wakefulness, a state of physical and mental rest characterised by the temporary detachment of consciousness and will, by the slowing down of neurovegetative functions and the partial interruption of the sensory-motor relations of the subject with the environment. An appropriate sleep is biologically necessary to support life. The physical and mental health condition of the person depends on the quality and duration of sleep.

The International classification of sleep disorders (ICSD 2005) gathers more than 90 of them. The most common sleep diseases can be distinguished into dyssomnias, parasomnias and breathing-related sleep disorders.

Dyssomnias are disorders that hinder the individual from falling asleep or cause early awakening and they are characterised by dysfunctional quality, quantity or times of sleep. Particularly known among dyssomnias is insomnia, characterised by inability to fall asleep. Insomnia is associated to poor daytime functioning, with symptoms such as tiredness, irritability, learning difficulty, lack of memory consolidation and marked loss of interest to carry out daily chores. Insomnia lasting for more than a few nights in a row can become "chronic" and cause a sleep deficit which is extremely harmful to the health of the insomniac. Parasomnias usually occur in the non-REM sleep stage and they are mainly related to psychological sleep and dream disorders.

Although there is no unique solution for sleep cycle disorders/dysfunctions, there is a variety of possible remedies available on the market, some from natural sources and others from pharmaceutical research. Phytocompounds, plant extracts and melatonin are examples of "natural" remedies. Barbiturates, benzodiazepines, neuroleptics, non-benzodiazepine hypnotics and pyrazolopyrimidines are, however, the categories of psychopharmaceuticals that are often administered for sleep disorders.

Scientific research has shown that the treatments of sleep disorders proposed up to now have drawbacks, such as: i) poor or partial efficacy, in particular of phytocompounds or natural substances; ii) time-induced tolerance and/or addiction (i.e. loss of response from the body to the drug), as in the case of benzodiazepines and non-benzodiazepine hypnotics; iii) dependence, as in the case of benzodiazepines and non-benzodiazepine hypnotics; iv) moderate to severe adverse effects, as in the case of barbiturates (e.g. intoxication, cardiorespiratory depression); v) no possibility of being used by paediatric subjects, as in the case of psychopharmaceuticals.

The technical problem addressed and solved by the present invention lies in providing effective compositions without adverse effects for use in a therapeutic and non-therapeutic method for the treatment of diseases, symptoms and/or disorders associated with one or more sleep cycle dysfunctions (dyssomnias and/or parasomnias), in particular for use in the simultaneous treatment of disorders both in the NON-REM stage of sleep and disorders in the REM stage of deep sleep such as, for example, early awakening and/or interruption of sleep by one or more nocturnal awakenings.

In order to overcome said technical problems, following an intense research the Applicant developed compositions (compositions of the invention) comprising (a) an extract of *Eucommia ulmoides* and one or more from among: (b.1) saffron (extract of *Crocus sativus* stigmas) comprising safranal and (b.2) an extract of *Magnolia officinalis* and/or *Magnolia champaca* comprising honokiol and, optionally, (c) magnesium.

Said compositions of the invention, when administered to a subject in need, are capable of treating in an effective, rapid and, furthermore, without adverse effects the diseases, the symptoms and/or the disorders caused by or deriving from a sleep cycle dysfunction, such as, for example, insomnia, inability to fall asleep, difficulty in falling asleep, early awakening, interruption of deep sleep by one or more nocturnal awakenings and excessive daytime sleepiness.

Said therapeutic or non-therapeutic treatment activity is due to the specific and innovative combination of two or more components (or active ingredients) present in the composition of the invention ((a) and (b.1) and/or (b.2) and, optionally, (c), as defined in the present description), given that each component acts on a different stage of the sleep cycle, providing highly effective action throughout the sleep cycle. In particular, the extract of *Eucommia ulmoides* (a) has a sedative action, the saffron comprising safranal (b.1) has a relaxing action by slowing the heart rate (bradycardic activity) which induces the gradual transition from wakefulness to sleep, the extract of *Magnolia officinalis* and/or *Magnolia champaca* comprising honokiol (b.2) has a relaxing action and an action of inducing the sleep stage, magnesium (c) has a relaxing action by reducing tiredness and fatigue.

Consequently, the compositions of the invention are capable of simultaneously treating both the disorders in the NON-REM stage of sleep and the disorders in the REM stage of deep sleep.

Furthermore, the specific combination of two or more components present in the composition of the invention ((a) and (b.1) and/or (b.2) and, optionally, (c)) is particularly effective in the treatment of sleep disorders thanks to a synergistic effect or an increase in the treatment activity of the composition with respect to the activity of the components taken individually and/or thanks to a modulation effect of a wider set of sleep disorders with respect to the activity of the individuals components.

Scientific research has shown that subjects with sleep disorders often have high levels of arousal (hyperarousal), both during the day and in the evening. Hyperarousal is defined as a state of activation of cognitive and physiological functions and it may result in long latency of the sleep stage (Riemann et al., 2010; model of hyperarousal in insomnia and disturbed night sleep). Thus, subjects with difficulty in the sleep stage due to high levels of arousal may benefit from compositions like the one of the present invention capable of reducing cognitive and physiological activation during the evening hours.

In addition, the compositions of the invention can be used by a large population of subjects, from paediatric age up to the senility stage in adult subjects, and in pregnant or breastfeeding women.

Furthermore, according to a preferred aspect of the invention, the present invention provides compositions which are cost-effective given that the presence of several active components acting on the aforementioned sleep disorders allows to use saffron (extract of *Crocus sativus* stigmas) with a lower titre of safranal, allowing a more competitive and accessible cost of production of the compositions of the invention, particularly for subjects in senility stage.

Lastly, in an embodiment, the present invention provides solid form compositions for oral administration formulated so that (a) the extract of *Eucommia ulmoides* is released over a prolonged period of time (delayed release, i.e. from 1.5 hours to 8 hours) after the administration of the composition to a subject and (b.1) saffron, if present, and/or (b.2) the extract of *Magnolia officinalis* and/or *Magnolia champaca*, if present, are each released over a shorter time with respect to (a) (fast and/or intermediate release).

Said modulated and differentiated release formulation of the various components (or active ingredients) of the composition of the invention allows each component to perform its own action in a different stage of the sleep cycle, making the composition of the invention particularly effective both in the NON-REM stage of sleep and in the REM stage of deep sleep. Furthermore, the controlled release of the active components improves the absorption and tolerability of the various components by the organism, favouring both relaxation and continuity of sleep and making the sleep of the subject restorative.

These and other objects which will be clear from the detailed description that follows, are achieved by the compositions and mixtures of the present invention thanks to the technical characteristics claimed in the attached claims.

FIGURES

FIG. 1: flow chart of the clinical trial.

DETAILED DESCRIPTION OF THE INVENTION

Forming an object of the present invention is a composition (pharmaceutical composition, medical device composition or dietary supplement, in short, composition of the invention) comprising (I) and, optionally, (II), wherein (I) is a mixture (in short, mixture of the invention) comprising or, alternatively, consisting of (a) and (b), wherein (a) is an extract of *Eucommia ulmoides* (Oliv.) and (b) is at least one further component (or active component) selected from among the group comprising or, alternatively, consisting of:

(b.1) a saffron (L.) comprising safranal, (b.2) an extract of *Magnolia officinalis* (Rehder & Wilson) and/or *Magnolia champaca* (L., Baill. formerly Pierre) comprising honokiol and (b.3) a mixture of said (b.1) and (b.2);

and wherein (II) is at least one food or pharmaceutical grade additive and/or excipient.

In short, the mixture of the present invention may comprise or, alternatively, consist of (a) and (b.1) or (a) and (b.2) or, as preferred embodiment, (a) extract of *Eucommia ulmoides*, (b.1) saffron comprising safranal and (b.2) extract of *Magnolia officinalis*, as defined in detail in the present description.

*Eucommia ulmoides* (Oliv.), also known in Chinese as "Du Zhong", is a plant belonging to the Eucommiaceae family containing a variety of components (about 112) such as phenols, steroids (phytoestrogens), polysaccharides (eucommans A and B) and flavonoids (among the most important of which rutin and quercetin).

*Eucommia ulmoides*, or an extract thereof, is considered a sedative capable of increasing the time, latency and quality of sleep.

The extract of *Eucommia ulmoides* (a) used in the present invention is preferably obtained through the extraction of the bark according to methods known to the man skilled in the art. For example, said extraction is carried out with water or hydroalcoholic solvent, such as water and ethanol. According to a known method, the extract of *Eucommia ulmoides* (a) can be obtained by pre-treating the *Eucommia ulmoides* bark by sorting and washing, extracting said pre-treated material with water to obtain an extraction liquid. Said extraction liquid is subsequently dried (spray drying) and the obtained dry extract is crushed and sieved to obtain a fine powder, which is lastly mixed to obtain the desired extract of *Eucommia ulmoides*.

The saffron comprising safranal (b.1) used in the present invention is preferably obtained through extraction from stigmas of the flower of *Crocus sativus* L. (or saffron crocus), preferably from dried stigmas, according to methods known to the man skilled in the art. For example, said extraction is carried out with hydroalcoholic solvent, such as water and ethanol. *Crocus sativus* is a plant of the Iridaceae family that grows up to 20-30 cm and produces up to four flowers, each with three deep crimson-coloured stigmas.

According to a known method, saffron comprising safranal (b.1) can be obtained through the extraction of Iridaceae *Crocus sativus* L. using a hydroalcoholic extraction in which ethanol is present (the final product has traces of ethanol <5000 ppm). The extraction step can be followed by the steps of filtration, concentration under vacuum, pasteurisation, spray drying with maltodextrin, addition of additives or excipients, mixing and/or sieving.

Saffron is considered to be a bradycardic with a muscle-relaxant cardiac action capable of lowering blood pressure, in particular thanks to the presence of safranal in saffron.

*Magnolia officinalis* (Rehder & Wilson) and *Magnolia champaca* (L. Baill. formerly Pierre) are plants belonging to the *Magnolia* family. *Magnolia officinalis* and *Magnolia champaca*, and in particular their bark, contain phenolic compounds including honokiol, which is known to interact with GABA A receptor and with cortisol hormone with a potential muscle relaxant and anxiolytic effect.

The extract of *Magnolia officinalis* and/or *Magnolia champaca* comprising the honokiol (b.2) used in the present invention is preferably obtained through the extraction of the bark, leaves and/or flowers, more preferably of the bark, according to methods known to the man skilled in the art. For example, said extraction is carried out with hydroalcoholic solvent, such as water and ethanol.

According to a known method, the extract of *Magnolia officinalis* and/or *Magnolia champaca* (b.2) can be obtained by pre-treating the raw material of *Magnolia officinalis* and/or *Magnolia champaca* by sorting and washing, extracting said pre-treated material with hydroalcoholic solvent (i.e. hot water and ethanol) to obtain an extraction liquid. Said extraction liquid is subsequently dried (spray drying)

and the obtained dry extract is crushed and sieved to obtain a fine powder, which is lastly mixed to obtain the desired extract of *Magnolia officinalis* and/or *Magnolia champaca*.

According to an embodiment, in the composition of the invention comprising (a) and (b.1) and/or (b.2) and, optionally, (c), as defined in the present description, said (b.1) saffron, preferably such as dry extract of *Crocus sativus* stigmas, comprises safranal at a % by weight comprised in a range from 0.01% to 1.5% with respect to the total weight of (b.1), preferably comprised from 0.05% to 1%, more preferably comprised from 0.1% to 0.5%, more preferably about 0.3%.

Advantageously, (b.1) is saffron such as dry extract of *Crocus sativus* stigmas comprising safranal at a % by weight of about 0.3% with respect to the total weight of the dry extract of saffron.

Furthermore, said (b.1) may comprise crocins and/or picrocrocins at a % by weight comprised in a range from 0.1% to 20% with respect to the total weight of said (b.1), preferably comprised from 0.5% to 10%, more preferably comprised from 0.8% to 5%.

According to an embodiment, in the composition of the invention comprising (a) and (b.1) and/or (b.2) and, optionally, (c), as defined in the present description, said (b.2) is a dry extract of bark, leaves and/or flowers of *Magnolia officinalis* and/or *Magnolia champaca*, preferably dry extract of bark, more preferably dry extract of *Magnolia officinalis* bark, comprising honokiol at a % by weight comprised in a range from 0.1% to 10% with respect to the total weight of (b.2), preferably comprised from 1% to 5%, more preferably comprised from 1.5% to 2.5%, preferably about 2%.

Advantageously, (b.2.) is a dry extract of *Magnolia officinalis* bark comprising honokiol at a % by weight of about 2% with respect to the total weight of dry extract of (b.2).

According to an embodiment, the composition of the invention comprises said (I) mixture comprising or, alternatively, consisting of: (a) extract of *Eucommia ulmoides*, preferably dry extract of bark, and (b.1) saffron, preferably such as dry extract of *Crocus sativus* stigmas, comprising safranal at % by weight comprised from 0.1% to 0.5% with respect to the total weight of (b.1), preferably about 0.3%.

According to an embodiment, the composition of the invention comprises said (I) mixture comprising or, alternatively, consisting of: (a) extract of *Eucommia ulmoides*, preferably dry extract of bark, and (b.2) extract of *Magnolia officinalis* and/or *Magnolia champaca*, preferably dry extract of bark, comprising honokiol at % by weight comprised from 1.5% to 2.5% with respect to the total weight of (b.2), preferably about 2%.

According to a preferred embodiment, the composition of the invention comprises said (I) mixture comprising or, alternatively, consisting of: (a) extract of *Eucommia ulmoides*, preferably dry extract of bark; (b.1) saffron, preferably such as dry extract of *Crocus sativus* stigmas, comprising safranal at % by weight comprised from 0.1% to 0.5% with respect to the total weight of (b.1), preferably about 0.3%; and (b.2) extract of *Magnolia officinalis* and/or *Magnolia champaca*, preferably dry extract of bark, more preferably dry extract of *Magnolia officinalis* bark, comprising honokiol at % by weight comprised from 1.5% to 2.5% with respect to the total weight of (b.2), preferably about 2%.

According to more preferred embodiment, the composition of the invention comprises said (I) mixture comprising or, alternatively, consisting of: (a) dry extract of *Eucommia ulmoides* bark, (b.1) saffron such as dry extract of *Crocus sativus* stigmas comprising safranal at % by weight of about 0.3% with respect to the weight of (b.1); and (b.2) dry extract of *Magnolia officinalis* bark comprising honokiol at % by weight of about 2% with respect to the total weight of (b.2).

According to a further embodiment, in the composition of the invention comprising (a) and (b.1) and/or (b.2), as defined in the present description, the mixture (I) further comprises (c) a magnesium, preferably said magnesium is present in the form of magnesium oxide.

Advantageously, the composition of the invention comprises (a), (b.1), (b.2) and (c).

According to a preferred embodiment, the composition of the invention comprises said (I) mixture comprising or, alternatively, consisting of: (a) dry extract of *Eucommia ulmoides* bark, (b.1) saffron such as dry extract of *Crocus sativus* stigmas comprising safranal at % by weight of about 0.3% with respect to the weight of (b.1); and (b.2) dry extract of *Magnolia officinalis* bark comprising honokiol at % by weight of about 2% with respect to the total weight of (b.2); and (c) magnesium oxide (MgO).

Forming an object of the present invention is the composition of the invention comprising (a) and (b.1) and/or (b.2) and, optionally, (c) according to any one of the embodiments reported in the present description, wherein the composition is for use as medicament.

Forming an object of the present invention is the composition of the invention comprising (a) and (b.1) and/or (b.2) and, optionally, (c) according to any one of the embodiments reported in the present description, wherein the composition is for use in a method for preventive and/or curative treatment of at least one disease, symptom and/or disorder associated with a sleep cycle dysfunction in a subject in need; preferably wherein said at least one disease, symptom and/or disorder is selected from among insomnia, inability to fall asleep, difficulty in falling asleep, early awakening, interruption of deep sleep by one or more nocturnal awakenings and excessive daytime sleepiness (EDS).

Advantageously, the composition of the invention is for use in a method for the simultaneous preventive and/or curative treatment of at least one disorder of the NON-REM stage of sleeping and at least one disorder of the REM stage of deep sleep, such as early awakening and interruption of sleep by one or more nocturnal awakenings.

Forming an object of the present invention is a method for the preventive and/or curative treatment of a disease, symptom and/or disorder associated with a sleep cycle dysfunction, in particular insomnia, inability to fall asleep, difficulty in falling asleep, early awakening, interruption of sleep by one or more nocturnal awakenings and excessive daytime sleepiness (EDS), which provides for the use (or administration) of the composition of the invention at a therapeutically effective amount to a subject in need.

In the present application, the term sleep cycle dysfunction (or sleep disorder) refers to a wide class of disorders such as: dyssomnias like insomnia, hypersomnia (sleep disorders characterised by excessive daytime sleepiness (EDS)), sleep disorder of the circadian rhythm and dyssomnias not otherwise specified; parasomnias such as nightmare disorder, night terror disorder, sleepwalking disorder and parasomnias not otherwise specified; sleep disorders related to another mental disorder such as insomnia related to another mental disorder; sleep disorders due to a general medical condition, in particular sleep disorders associated with diseases such as neurological disorders, neuropathic pain, heart and lung diseases; sleep motor disorders such as restless leg syndrome (RLS), periodic limb movements (PLM) and bruxism; jet lag syndrome; sleep quality disorder (which makes sleep perceived by the subject as a sleep that does not fully restore the physical and mental condition of the subject).

In the present application the expression insomnia is used to indicate a sub-class of sleep disorders characterised by inability to fall asleep despite the organism's actual physiological need of it. From a symptomatic standpoint, there are three types of insomnia: initial insomnia, i.e. difficulty to fall asleep, intermittent or middle or lacunary insomnia characterised by frequent awakening at night, terminal insomnia, characterised by early awakening with inability to fall asleep.

The composition of the invention may be for use in a method for the treatment of disease, symptom and/or disorder associated with sleep cycle dysfunctions as defined above, when administered to a subject as the single composition capable of treating said disease, symptom and/or disorder as well as when administered as an adjuvant of at least another composition capable of treating said disease, symptom and/or disorder.

According to an embodiment, the composition of the invention for "daily intake units" comprises: (a) extract of *Eucommia ulmoides*, preferably dry extract of bark, at an amount comprised from 50 mg to 350 mg, preferably comprised from 100 mg to 300 mg, more preferably comprised from 150 mg to 250 mg; (b.1) saffron, preferably such as dry extract of *Crocus sativus* stigmas comprising safranal at % by weight comprised from 0.1% to 0.5% with respect to the total weight of (b.1), preferably about 0.3%, at an amount comprised from 5 mg to 65 mg, preferably comprised from 20 mg to 40 mg, more preferably comprised from 25 mg to 35 mg; (b.2) extract of *Magnolia officinalis* and/or *Magnolia champaca*, preferably dry extract of *Magnolia officinalis* bark, comprising honokiol at % by weight comprised from 1.5% to 2.5% with respect to the total weight of (b.2), preferably about 2%, at an amount comprised from 50 mg to 350 mg, preferably comprised from 100 mg to 300 mg, more preferably comprised from 150 mg to 250 mg; and, optionally, (c) magnesium, preferably in the form of magnesium oxide, at an amount such as elemental magnesium comprised from 10 mg to 100 mg, preferably comprised from 30 mg to 70 mg, more preferably comprised from 45 mg to 65 mg.

Said "daily intake unit" of the composition of the invention may be administered to a subject in need by administering a single dosage form per day or by administering from 2 to 4 individual dosage forms per day, depending on the type of dosage form and the needs of the subject.

Advantageously, the composition of the invention comprising (a) and (b.1) and/or (b.2) and, optionally, (c) as defined in the present description, may further comprise a further component (or active component) (d) selected from among the group comprising or, alternatively, consisting of: vitamins of group B, C, D, E, organic and/or inorganic salts of magnesium, selenium, zinc, melatonin, valerian, free L-tryptophan, passiflora, lemon balm, hawthorn, chamomile, hops, griffonia, scutellaria, antioxidants and mixtures thereof.

The composition of the invention can be in solid dosage form, such as tablet, chewable tablet, capsule, lozenge, granules or powder, in semi-solid form, such as soft-gel, or in liquid form, such as solution, suspension, dispersion, emulsion or syrup; it is preferably in solid form, more preferably in form of tablet.

The composition of the invention can be formulated for oral (or gastroenteric), sublingual (or buccal) or transmucosal administration; advantageously it is formulated for oral administration, preferably for oral administration in solid form, more preferably for oral administration in solid form of tablet.

In an embodiment, the composition of the invention is formulated in solid form for oral administration, wherein said formulation comprises:
  (i) a first delayed release formulation comprising said (a) extract of *Eucommia ulmoides*, preferably dry extract of bark, wherein said extract (a) is released in the intestinal tract within a time comprised in a range from 1.5 hours to 8 hours after the administration of the composition of the invention to a subject, preferably comprised from 2 hours to 7 hours, more preferably comprised from 2.5 hours to 6 hours;
  (ii) at least one or two further formulations selected from among:
    (ii.i) a second immediate release formulation comprising said (b.1) saffron, preferably dry extract of *Crocus sativus* stigmas, comprising safranal at % by weight comprised from 0.01% to 1.5% with respect to the total weight of (b.1), preferably comprised from 0.05% to 1%, more preferably comprised from 0.1% to 0.5% and, optionally, said (c) magnesium, preferably magnesium oxide; wherein said (b.1) and, optionally, said (c) are released in the gastric mucosa within a time range comprised from 5 minutes to 20 minutes after the administration of the composition to said subject, preferably comprised from 5 minutes to 15 minutes, more preferably comprised from 5 minutes to 10 minutes; and
    (ii.ii) a third intermediate release formulation comprising said (b.2) extract of *Magnolia officinalis* and/or *Magnolia champaca*, preferably dry extract of bark, comprising honokiol at a % by weight comprised from 0.1% to 10% with respect to the total weight of (b.2), preferably comprised from 1% to 5%, more preferably comprised from 1.5% to 2.5%; wherein said extract (b.2) is released in the first intestinal tract within a time comprised in a range from 20 minutes to 120 minutes or from 20 minutes to 90 minutes after the administration of the composition to said subject, preferably comprised from 20 minutes to 60 minutes, more preferably comprised from 20 minutes to 45 minutes.

In a preferred embodiment, the composition of the invention is formulated in solid form for oral administration, wherein said formulation comprises:
  (i) said first delayed release formulation comprising said (a) dry extract of *Eucommia ulmoides* bark, wherein said extract (a) is released in the intestinal tract within a time comprised in a range from 1.5 hours to 8 hours after the administration of the composition of the invention to a subject, preferably comprised from 2 hours to 7 hours, more preferably comprised from 2.5 hours to 6 hours; and
  (ii.i) said second immediate release formulation comprising said (b.1) saffron, such as dry extract of *Crocus sativus* stigmas, comprising safranal at % by weight comprised from 0.1% to 0.5% with respect to the total weight of (b.1), and, optionally, said (c) magnesium, preferably magnesium oxide; wherein said (b.1) and, optionally, said (c) are released in the gastric mucosa within a range comprised from 5 minutes to 45 minutes or from 5 minutes to 20 minutes after the administration of the composition to said subject, preferably comprised from 5 minutes to 15 minutes, more preferably comprised from 5 minutes to 10 minutes; and (ii.ii) said third intermediate release formulation comprising said (b.2) dry extract of *Magnolia officinalis* and/or *Magnolia champaca* bark, comprising honokiol at a % by weight comprised from 1.5% to 2.5% with respect to the total weight of (b.2); wherein said extract (b.2) is released in the first intestinal tract within a time comprised in a range from 20 minutes to 120 minutes or from 20 minutes to 90 minutes after the administration of the composition to said subject, preferably comprised from 20 minutes to 60 minutes, more preferably comprised from 20 minutes to 45 minutes.

Preferably, said (ii.i) second immediate release formulation comprising said (b.1) saffron, preferably such as dry extract of *Crocus sativus* stigmas, comprising safranal at % by weight comprised from 0.1% to 0.5% with respect to the total weight of (b.1), preferably at about 0.3%, comprises said (c) magnesium, preferably magnesium oxide.

In a more preferred embodiment, the composition of the invention is formulated for oral administration, in multilayer solid form comprising:

(I) a first layer comprising or, alternatively, consisting of said (ii.i) second immediate release formulation comprising (b.1) and, optionally, (c);

(II) a second layer, preferably at least partially underlying the first layer, comprising or, alternatively, consisting of said (i) first delayed release formulation comprising (a); and (Ill) a third layer, preferably at least partially underlying the second layer, comprising or, alternatively, consisting of said (ii.ii) third intermediate release formulation comprising said (b.2).

Advantageously, the composition of the invention is a multilayer tablet wherein said (II) second layer is arranged between the (I) first layer and the (III) third layer.

In an embodiment, preferably of multilayer tablet, in the composition of the invention comprising (a) and (b.1) and/or (b.2) and, optionally, (c)—said first delayed release formulation comprises: said (a) dry extract of *Eucommia ulmoides* bark (50-60% by weight with respect to the total weight of (i)), hydroxypropyl methylcellulose with molecular weight between 1,000 and 4,000,000 (15-25% by weight with respect to the total weight of (i)) and microcrystalline cellulose (15-25% by weight with respect to the total weight of (i));

said (ii.i) second immediate release formulation, if present, comprises: said (b.1) saffron such as dry extract of *Crocus sativus* stigmas comprising safranal at a % by weight comprised from 0.1% to 0.5% with respect to the total weight of (b.1) ((b.1) 5-10% by weight with respect to the total weight of (ii.i)), crosslinked sodium carboxymethylcellulose (1-5% by weight with respect to the total weight of (ii.i)) and microcrystalline cellulose (40-50% by weight with respect to the total weight of (ii.i)) and, optionally, (c) magnesium (10-20% by weight as elemental magnesium with respect to the total weight of (ii.i));

said (ii.ii) third intermediate release formulation, if present, comprises: said (b.2) dry extract of *Magnolia officinalis* bark comprising honokiol at a % by weight comprised from 1.5% to 2.5% with respect to the total weight of (b.2) ((b.2) 50-60% by weight with respect to the total weight of (ii.ii)), crosslinked sodium carboxymethylcellulose (0.5 to 3% by weight with respect to the total weight of (ii.ii)), and microcrystalline cellulose (20-30% by weight with respect to the total weight of (ii.ii)).

In an embodiment, said second layer (II) comprising or, alternatively, consisting of said (i) first delayed release formulation comprising (a) extract of *Eucommia ulmoides*, is coated with a gastro-resistant coating or, alternatively, said gastro-resistant coating is present between said (II) second layer and said (I) first layer and/or between said (II) second layer and said (III) third layer.

In the embodiment in which the composition of the invention is formulated in two or three differentiated release formulations, preferably in the form of a multilayer tablet, the delayed release of (a) extract of *Eucommia ulmoides* causes the appearance of plasma peaks (a) delayed and prolonged over time. Said slow release of (a) favours the sedative action of the composition of the invention in all stages of the sleep cycle, avoiding the nocturnal awakenings, given that the prolonged contact of (a) with the intestinal mucosa ensures the presence of (a) in the blood for most of the time of the sleep cycle. Furthermore, the slow release of (a) may lead to a reduction in the effects of first hepatic passage.

Being a bradycardic with cardiac muscle relaxant action, the (b.1) saffron comprising safranal, was inserted into the immediate release formulation (ii.i) (for example, in the (I) first layer of multilayer tablet); this results in relaxation of the individual due to the slowing of heart rate (bradycardic activity) allowing the gradual transition from wakefulness to sleep (NON-REM stage of sleep).

The same formulation (ii.i) with immediate release (for example, in the (I) first layer of multilayer tablet) can also comprise (c) magnesium (e.g. magnesium oxide), which contributes to the reduction of tiredness and fatigue, thus favouring relaxation. In addition, (c) magnesium protects the heart and blood circulation against the effects of stress.

The presence of (b.2) extract of *Magnolia officinalis* and/or *Magnolia champaca*, preferably extract of bark, in the formulation (ii.ii) with intermediate release (for example, in the (III) third layer of multilayer tablet) guarantees the appearance of plasma peaks of (b.2) in advance with respect to those that would occur with a longer product break down (or release) time, thus favouring the induction of sleep in a short time.

Said modulated and differentiated release formulation of the individual components, preferably of multilayer tablet comprising (a), (b.1), (b.2) and, optionally, (c), allows the composition of the invention to act through of the extract of *Magnolia* (b.2) on the induction of the sleep stage immediately after the relaxation given by saffron (b.1), starting to act already at the level of the gastric mucosa, and to act through the extract of *Eucommia ulmoides* (a) on the maintenance of the deep sleep stage for a prolonged period of time.

Furthermore, the present invention relates to the non-therapeutic use of the composition of the invention according to the various embodiments described in the present description, wherein said use is for a non-therapeutic treatment of sleep cycle improvement that allows the subjects using the composition of the invention to benefit from advantageous conditions with respect to inability or difficulty in falling sleeping, early awakening, interruption of sleep by one or more nocturnal awakenings and excessive daytime sleepiness.

Lastly, forming an object of the present invention is a pharmaceutical composition, medical device composition, nutraceutical composition, dietary supplement product or food for special medical purpose comprising or, alternatively, consisting of the composition of the present invention.

In the context of the present invention, the expression "medical device" is used according to the meaning laid down by the Italian Legislative Decree no 46, dated 24 Feb. 1997 (or according to the new Medical Devices Regulation (UE) 2017/745 (MDR)), i.e. it indicates a substance or another product, used alone or in combination, designated by the manufacturer to be used in humans for the diagnosis, prevention, control, therapy or attenuation of a disease, the product not exercising the main action, in or on the human body, for which it is designated, neither using pharmacological or immunology means nor by means of a metabolic process but the function thereof can be coadjuvated by such means.

For the sake of clarity, to achieve the object of the present invention, the components (or active components) of the (I) mixture of the present invention (a) and (b.1) and/or (b.2) and, optionally, (c) may also be administered separately (preferably within a time range of 30 minutes to 60 minutes) and in any order but, preferably, (a) and (b.1) and/or (b.2) and, optionally, (c) are administered to a subject simultaneously, even more preferably in a single composition to achieve a more rapid effect and for the ease of administration.

When the active ingredients (a) and (b.1) and/or (b.2) and, optionally, (c) are administered in a single composition, said single composition corresponds to the composition of the present invention.

The composition of the invention optionally comprises said (II) at least one pharmaceutical or food grade additive and/or excipient, i.e. a substance devoid of therapeutic activity suitable for pharmaceutical or food use. In the context of the present invention the acceptable ingredients for pharmaceutical or food use comprise all auxiliary substances known to the man skilled in the art such as, by way of non-limiting example, diluents, solvents (including water, glycerine, ethyl alcohol), solubilizers, thickeners, sweeteners, flavour enhancers, colourants, lubricants, surfactants, antimicrobials, antioxidants, preservatives, pH stabilizing buffers and mixtures thereof. Non-limiting examples of such substances are phosphate buffers, magnesium stearate, silicone dioxide, cross-linked sodium carboxymethylcellulose, microcrystalline cellulose, hydroxypropyl methylcellulose, natural or artificial flavours.

Unless specified otherwise, the expression "composition comprises a component at an amount comprised in a range from x to y" is used to indicate that said component may be present in the composition at all the amounts present in said range, even though not specified, extremes of the range comprised.

The term "therapeutically effective amount" refers to the amount of active compound/s eliciting the biological or medicinal response in a tissue, system, mammal, or human being that is sought and defined by an individual, researcher, veterinarian, physician, or other clinician or health worker.

According to the embodiments reported in the present description, the compositions of the present invention allow the therapeutic and non-therapeutic effective treatment of diseases, symptoms and/or disorders associated with sleep cycle dysfunctions. In particular, the compositions of the invention, preferably formulated with modulated release of the individual active components ((a), (b.1), (b.2) and/or (c)), ensure a relaxation of the treated subject in the short term which leads the subject to fall asleep rapidly and, furthermore, they guarantee the duration of deep sleep protecting the subject against nocturnal awakenings or early interruption of sleep. The compositions of the invention do not have any relevant adverse effects.

Experimental Part

Table 1 shows an embodiment of the composition of the invention comprising (a), (b.1), (b.2) and (c) formulated for oral administration in solid form of a three-layer tablet, including a first immediate release layer (layer I), a second delayed release layer (layer II) and third intermediate release layer (layer III).

TABLE 1

| | Ingredient | daily dose intake in mg |
|---|---|---|
| Immediate release layer I | (b.1) saffron (e.g. *Crocus sativus* stigmas) 0.3% safranal | 5-65 (safranal 0.02-0.2) |
| | (c) Magnesium oxide | 10-100 |
| | Microcrystalline cellulose | Q.S. |
| | Dicalcium phosphate | Q.S. |
| | Crosslinked sodium carboxymethylcellulose | Q.S. |
| | Silicon dioxide | Q.S. |
| | Stearate magnesium | Q.S. |
| | Yellow iron oxide | Q.S. |
| Delayed Release layer II | (a) extract of *Eucommia ulmoides* bark | 50-350 |
| | Dicalcium phosphate | Q.S. |
| | Microcrystalline cellulose | Q.S. |
| | Silicon dioxide | Q.S. |
| | Stearate magnesium | Q.S. |
| | Hydroxypropyl methylcellulose | Q.S. |
| Intermediate release layer III | (b.2) extract of *Magnolia officinalis* bark (e.g. 2% honokiol) | 50-350 (honokiol 1-7) |
| | Microcrystalline cellulose | Q.S. |
| | Crosslinked sodium carboxymethylcellulose | Q.S. |
| | Dicalcium phosphate | Q.S. |
| | Silicon dioxide | Q.S. |
| | Stearate magnesium | Q.S. |
| | Red iron oxide | Q.S. |
| | TOTAL | 1200 |

Break Down Test

A break down test is carried out on at least one composition according to the invention, comprising (a), (b.1), (b.2) and, optionally, (c) formulated in solid form of three-layer tablet for oral administration in order to analyse the differentiated modulated release of components (a), (b.1), (b.2) and, optionally, (c).

Sleep Quality Test

The quality of sleep can be measured by analysing various parameters: subjective parameters, such as the good quality of sleep, and objective parameters, such as the duration of sleep episodes, the number of early awakenings and the time of sleep.

In order to analyse the efficacy of at least one composition according to the invention in treating sleep disorders, the subjects administered with a composition of the invention, comprising (a), (b.1), (b.2) and, optionally, (c) formulated in solid form of three-layer tablet for oral administration, were required to fill out the following questionnaires:

Pittsburgh Sleep Quality Index (PSQI)
Pre-Sleep Arousal Scale (PSAS)
Insomnia Severity Index (ISI)
VAS for product satisfaction.
Pittsburgh Sleep Quality Index (PSQI) (Buysse et al., 1989; Chesson et al., 2000; Sateia et al., 2000). PSQI is one of the most widely used questionnaires in evaluating sleep quality. It was designed to provide a reliable, valid and standardized measure of sleep quality. The use of this tool is justified by the good psychometric properties that characterise it and by the presence of cut-off scores. The scale cut-off is represented by a score greater than 5, considered pathological.

Pre-Sleep Arousal Scale (PSAS) (Nicassio et al., 1985). PSAS is a questionnaire that can evaluate both the cognitive and somatic arousal. This scale consists of 16 items (8 for the somatic domain and 8 for the cognitive domain). Ratings range from 1 (not at all) to 5 (extremely), with a score range between 8 and 40, for each of the 2 domains.

Insomnia Severity Index (ISI) (Morin et al., 2011; Castronovo et al., 2016).

Initially called Sleep Impairment Index (Morin et al., 1993), the scale was subsequently validated and renamed the Insomnia Severity Index (ISI) (Bastien et al., 2001). The scale was validated in 2011 by the Morin group (Morin et al., 2011) and the cut-off was set to 10. In Italian, the scale was validated in 2016 by Castronovo, Galbiati, Marelli and their colleagues (Castronovo et al., 2016). This tool, consisting of 5 questions, is used to determine the severity and impact of insomnia on the patient's life. The ISI is a scale consisting of 7 items, through which the patient assesses the difficulty in falling asleep in terms of severity (divided into three different areas: "Difficulty in falling asleep," "difficulty maintaining sleep" and "early-awakening problem,"), degree of interference with daytime efficiency, evidence of such deterioration for others, degree of discomfort, and global satisfaction with one's sleep. Ratings are distributed on a Likert scale from 0 to 4. To calculate the score, only the values of the 5 questions are added together for a total of 7 items. The total score ranges from 0 to 28 and it is evaluated as follows: 0-7: absence of clinically significant insomnia; 8-14: insomnia below critical threshold; 15-21: clinical insomnia (medium severity); 22-28: clinical insomnia (severe). Please see the appendix for the full questionnaire.

Visual Analogic Scale (VAS).

Continuous self-assessment scale of product satisfaction. It consists of a segment (100 mm) on which the subject must indicate the perceived level of satisfaction between the two extremes 0="not at all" and 100="extreme".

1. Type of trial: interventional, double-blind, randomised (1:1 ratio): Composition of the invention vs. placebo.
2. Objectives:
2.1. Primary objective
A) Evaluating changes from baseline in Pittsburgh Sleep Quality Index (PSQI) to end-of-trial visit (day 28) in adult subjects with disturbed nocturnal sleep and poor-quality sleep treated with composition of the invention vs placebo.
2.2. Secondary objectives
Evaluating changes from baseline of the score in scale vs. placebo
  (a) Pre sleep Arousal Scale (PSAS),
  (b) Insomnia Severity Index (ISI), and
  (c) Visual Analogic Scale (VAS)
at the end-of-trial visit in adult subjects with disturbed nocturnal sleep and poor-quality sleep treated with composition of the invention.
  d) evaluating changes from baseline to sleep diary versus placebo (total sleep time (TST); sleep latency (SL), sleep efficiency (SE %) at the end-of-trial visit in adult subjects with disturbed nocturnal sleep and poor-quality sleep treated with composition of the invention.

3. Sample: 68 adult subjects.
3.1. Inclusion criteria
1. Men and women subjects 18 years and older and 65 years or younger.
2. Pittsburgh Sleep Quality Index (PSQI) score >5.
3. Pre-Sleep Arousal Scale (PSAS) score >15 in least one of the two domains.
4. Ability to understand and sign informed consent.
4. Treatments
4.1. Product:
composition of the invention (in brief, composition): according to Table 1;
placebo: an oral formulation of an inert tablet.
4.2 Method A tablet of composition (1200 mg) or placebo is administered orally. The product under trial will be taken in the evening 30 minutes-60 minutes before bedtime. The treatment will last from day 1 to day 27 (the unutilised product will be collected on day 28).

The following pharmacological therapies are prohibited: benzodiazepines, z-drugs (zopiclone, eszopiclone, zaleplon and zolpidem), antidepressants.

5. Visits
5.1. Visit 1 (baseline) at Centro di Medicina del sonno—UO Neurologia OSRT (DAY 1) The subjects sign informed consent and, once the inclusion and exclusion criteria have been verified, they are assigned to the double-blind treatment group (randomisation), the clinical history, concomitant therapies, demographic data are collected, a physical examination (vital signs, weight and height for BMI calculation) and a urine pregnancy test are performed.

All subjects fill out the following questionnaires at baseline:
Pittsburgh Sleep Quality Index (PSQI)
Pre-Sleep Arousal Scale (PSAS)
Insomnia Severity Index (ISI)

Throughout the course of the trial, subjects fill out a sleep diary.

The trial product is delivered and intake modes are explained.

5.2. Visit 2 phone contact (DAY 14)
All subjects are contacted by telephone to evaluate treatment compliance and possible adverse events.

5.3. Visit 3 at Centro di Medicina del sonno—UO Neurologia OSRT (DAY 28)

All subjects undergo a physical examination (vital signs, weight and height for BMI calculation).

All subjects fill out the PSQI, PSAS, ISI and VAS questionnaires and the filled-out sleep diary is collected from the subjects. Furthermore, the unused product is collected.

The following are evaluated: efficacy, treatment compliance and possible adverse events.

5.4. Visit 4 follow-up contact by telephone (DAY 35)
All subjects are contacted by telephone effects from suspension, the beneficial effect of the treatment and possible adverse events.

6. Data analysis
6.1. Randomisation list
The blind randomisation list was created for participating investigators. The sequence that the patient to perform is kept in a single envelope (one per patient), sealed and filed in the trial folder and it is opened only once the patient has been enrolled/randomised.

6.2. Statistical Analysis
The primary objective of the trial is to evaluate the change from baseline to trial end in the mean PSQI (primary efficacy variable) score in a direct comparison between active and placebo. To this end, the primary efficacy variable analysis is performed using a linear model (ANCOVA) with the treatment and PSQI baseline score as covariant and the difference in PSQI score with respect to the baseline as dependent variable. Results are reported as mean differences between treatments with 95% confidence intervals and two-tailed probability values.

Just like the primary endpoint analysis, analysis of all secondary efficacy parameters is performed using an ANCOVA model with treatment and baseline measurements as covariant and change with respect to the baseline as dependent variable. Results are reported as mean differences between treatments with 95% confidence intervals and two-tailed probability values.

The same statistical approach (ANCOVA) is used for the analysis of changes from baseline to intermediate visits (visit 3).

Since all analyses performed on secondary efficacy endpoints and any intermediate visits (visit 3) are only exploratory or supportive of the results obtained on the primary endpoint, no significant level adjustment is made to account for multiple comparisons.

Missing data on the primary efficacy endpoint and all secondary efficacy endpoints are imputed using the last observation carried forward (LOCF). All efficacy analyses are performed on the Intention To Treat (ITT) population. The analysis of the primary efficacy variable is also performed on the Per Protocol (PP) population to evaluate the robustness of the results while the tolerability data are evaluated on the Safety population. SAS software version 9.4 is used for statistical analysis and data management.

The invention claimed is:

1. A composition in the form of a three layer tablet comprising:
   (a) a first layer comprising 50 mg to 350 mg dry extract of *Eucommia ulmoides* bark,
   (b) a second layer comprising a dry extract of *Crocus sativus* stigmas, wherein the second layer comprises 0.1% to 0.5% safranal by weight, and
   (c) an a third layer comprising a dry extract of: (i) *Magnolia officinalis* bark and/or (ii) *Magnolia champaca* bark, wherein third layer comprises 1.5% to 2.5% honokiol by weight;
   wherein the tablet formulated for oral administration and optionally further comprises at least one food grade or pharmaceutical additive and/or excipient.

2. The composition according to claim 1, wherein tablet further comprises magnesium.

3. The composition according to claim 1, wherein:
   (i) the dry extract of *Eucommia ulmoides* bark is released into the intestinal tract of a subject 1.5 hours to 8 hours after administration of the composition to said subject;
   (ii) the dry extract of *Crocus sativus* stigmas is released into the gastric mucosa of the subject in 5 minutes to 45 minutes after the administration of the composition to said subject;
   (iii) the dry extract of: (i) *Magnolia officinalis* bark and/or (ii) *Magnolia champaca* bark is released in the intestinal tract of the subject in 20 minutes to 120 minutes after the administration of the composition to said subject.

4. The composition of claim 1, wherein the second layer further comprises magnesium.

5. The composition according to claim 1, wherein, in the tablet, the third layer is under the second layer and the first layer is under the third layer.

6. A method of treating a subject for a sleep cycle dysfunction comprising administering an effective amount of the composition according to claim 1 to the subject.

7. The method of claim 6, wherein the subject has insomnia, inability to fall asleep, difficulty in falling asleep, early awakening, interruption of deep sleep by one or more nocturnal awakenings, and excessive daytime sleepiness.

8. The method of claim 6, wherein said subject has at least one disorder of the NON-REM stage of sleep and at least one disorder of the REM stage of deep sleep.

9. The method of claim 6, wherein the tablet further comprises magnesium.

10. The method of claim 6, wherein:
    (i) the dry extract of *Eucommia ulmoides* bark is released into the intestinal tract of a subject 1.5 hours to 8 hours after administration of the composition to said subject;
    (ii) the dry extract of *Crocus sativus* stigmas is released into the gastric mucosa of the subject in 5 minutes to 45 minutes after the administration of the composition to said subject;
    (iii) the dry extract of: (i) *Magnolia officinalis* bark and/or (ii) *Magnolia champaca* bark is released in the intestinal tract of the subject in 20 minutes to 120 minutes after the administration of the composition to said subject.

11. The method of claim 6, wherein the second layer further comprises magnesium.

12. The method of claim 6, wherein, in the tablet, the third layer is under the second layer and the first layer is under the third layer.

* * * * *